United States Patent
Kim

(10) Patent No.: US 12,144,954 B2
(45) Date of Patent: Nov. 19, 2024

(54) TIP FOR INJECTING TATTOO DYE

(71) Applicant: ADDOBIO, Seoul (KR)

(72) Inventor: Changok Kim, Gunpo (KR)

(73) Assignee: ADDOBIO, Seoul (KR)

( * ) Notice: Subject to any disclaimer, the term of this patent is extended or adjusted under 35 U.S.C. 154(b) by 165 days.

(21) Appl. No.: 17/792,381

(22) PCT Filed: Feb. 21, 2020

(86) PCT No.: PCT/KR2020/002549
§ 371 (c)(1),
(2) Date: Jul. 12, 2022

(87) PCT Pub. No.: WO2021/167143
PCT Pub. Date: Aug. 26, 2021

(65) Prior Publication Data
US 2023/0050610 A1    Feb. 16, 2023

(51) Int. Cl.
*A61M 37/00* (2006.01)
(52) U.S. Cl.
CPC .............. *A61M 37/0084* (2013.01)
(58) Field of Classification Search
CPC .......... A61M 37/0076; A61M 37/0084; A61M 39/22; A61M 39/24; A61M 5/1782; A61M 5/204; A61M 5/2046; A61M 5/2053; A61M 5/30; A61M 5/3007; A61M 2005/3128; A61M 11/00; A61B 2018/263
See application file for complete search history.

(56) References Cited

U.S. PATENT DOCUMENTS

2018/0154082 A1*    6/2018    Yoh ............... A61M 5/2046

FOREIGN PATENT DOCUMENTS

| KR | 101687199 | B1 | 12/2016 |  |
|---|---|---|---|---|
| KR | 101838631 | B1 | 4/2018 |  |
| KR | 101862201 | B1 | 5/2018 |  |
| KR | 10-20190049097 | * | 5/2019 | .......... A61M 5/3007 |
| KR | 1020190049097 | A | 5/2019 |  |
| KR | 1020190127008 | A | 11/2019 |  |
| KR | 20200015052 | A | 2/2020 |  |

* cited by examiner

*Primary Examiner* — Robert A Lynch

(57) ABSTRACT

The present invention relates to a tip for injecting a tattoo dye can inject a dye at high pressure without a needle, and thus can relieve pain of a person being tattooed, and has the effect of allowing tattooing to be hygienically performed.

7 Claims, 14 Drawing Sheets

TIP FOR INJECTING TATTOO DYE

TECHNICAL FIELD

The disclosure relates to a tip for injecting tattoo dye, and more particularly to a tip for injecting dye through a dye inject nozzle.

Background Art

With recent increase of interest in tattoos and exposure of the tattoos through many media, demand for the tattoos has been increased. A tattooing device is configured to inject dye into human skin so that the dye can be visually distinguished like various patterns or letters.

Conventionally, the tattooing device repeatedly performs operations of inserting a needle into the skin, injecting the dye into the skin, and then withdrawing the needle. Such a conventional tattooing device has been disclosed in Korean patent publication No. 2020-0015052 (published on Feb. 12, 2020).

However, the conventional tattooing device, in which the needle is inserted into the skin to inject the dye, have problems in that a person who is getting tattoo feels considerable pain, hygiene is poor, and tattoo results are different according to skill levels of a user who is using the tattooing device.

DISCLOSURE

Technical Problem

To solve the foregoing problems of a conventional tattooing device, an aspect of the disclosure is to provide a tip for injecting tattoo dye without a needle.

Technical Solution

According to an embodiment of the disclosure, there may be provided a tip for injecting tattoo dye, including: a pressure chamber configured to accommodate liquid therein; a window provided at a first side of the pressure chamber, and configured to allow a laser beam emitted from an outside to pass therethrough and reach the liquid accommodated in the pressure chamber; a membrane unit provided at the first side of the pressure chamber, and configured to seal the pressure chamber and be transformed by pressure generated as the liquid is irradiated with the laser beam; a dye chamber configured to accommodate tattoo dye, and including one side for fluid communication with the membrane unit; a dye supply unit configured to supply the dye to the dye loading space; a first valve configured to set whether to allow the dye to flow from the dye supply unit to the dye chamber; and an inject nozzle provided at one side of the dye chamber, and configured to inject the dye accommodated in the dye loading space.

Meanwhile, to inject the dye, the pressure chamber may be configured to be increased in pressure by laser pulses applied thereto from the outside, the membrane unit may be configured to be transformed to transfer the pressure to the dye chamber as the pressure chamber is internally increased in pressure, and the dye chamber may be configured to be internally increased in pressure by the membrane unit so that the dye can flow toward the inject nozzle and be injected.

Meanwhile, the dye chamber may include a channel formed at one side of an inner wall thereof and configured for fluid communication with the dye supply unit.

Meanwhile, the first valve may include an opening/closing portion to come into close contact with and seal an opening of the channel at a side of the inner wall, and the opening/closing portion may include an elastic material to be transformed by difference between the internal pressure of the dye chamber and the internal pressure of the channel.

Meanwhile, the dye chamber may be internally formed with a cylindrical space, the first valve may have a hollow shape and include an outer circumferential surface to come into close contact with an inner surface of the cylindrical space of the dye chamber, and the opening/closing portion may be configured to be transformed toward a central axis of the hollow.

Meanwhile, the tip for injecting tattoo dye may further include a second valve provided inside the dye chamber, and configured to set whether to allow the dye to flow toward the inject nozzle.

Meanwhile, the second valve may include a one-way valve.

Further, the tip for injecting tattoo dye may further include a stopper configured to press the second valve toward the inject nozzle so that the second valve can be locked in the dye chamber.

Further, the stopper may be internally formed with a hollow to allow the dye to move from an inside of the dye chamber to the inject nozzle.

Meanwhile, the dye supply unit may include a slider valve at one side.

Advantageous Effects

According to the disclosure, the tip for injecting tattoo dye according to the disclosure can inject the dye at high pressure without a needle, thereby having effects on relieving pain of a person who is getting tattoo, and carrying out a tattooing procedure hygienically.

Further, the tip for injecting tattoo dye according to the disclosure can inject a fixed amount of dye at each inject. In addition, the tip for injecting tattoo dye has an effect on preventing external foreign materials from being introduced thereinto through the inject nozzle.

MODE FOR INVENTION

Figure 1:
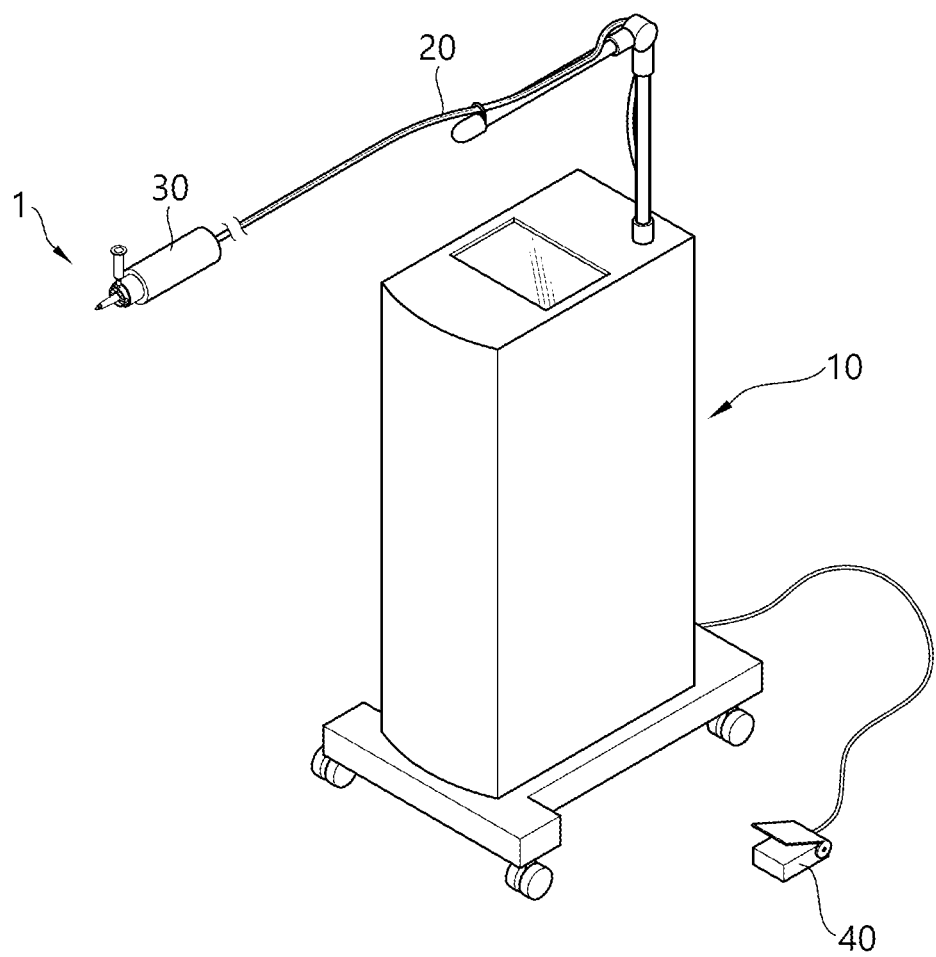
FIG. 1 is a perspective view of a tattooing device mounted with a tip for injecting tattoo dye according to the disclosure.

Hereinafter, a tip for injecting dye according to embodiments of the disclosure will be described in detail with reference to the dye inject tip. The names of elements used in the following description may be referred to as other names in the art. However, these elements may be considered as equivalent elements in alternative embodiments as long as they have functional similarity and identity. Further, the reference numerals of the elements are provided for the convenience of description. However, the elements indicated by the reference numerals in the drawings are not limited to the scope shown in the drawings. Similarly, even though some elements in the drawings are modified in alternative embodiments, these elements are considered as equivalent elements as long as they have functional similarity and identity. Further, when elements are regarded as elements that should be naturally included at the level of those skilled in the art, descriptions thereof will be omitted.

FIG. 1 is a perspective view of a tattooing device mounted with a tip 1 for injecting tattoo dye according to the disclosure.

As shown therein, the tip 1 for injecting tattoo dye according to the disclosure is connected to a laser generator and internally generates pressure based on a laser beam emitted from the outside, thereby injecting tattoo dye.

The tattooing device may include a main body 10, a foot switch 40, a cable 20, and a handpiece 30.

The main body 10 may include a controller, an interface, and a power supply. The controller may be configured to generate a laser beam in response to a user's input, and configured to control the pattern, cycle, number, etc. of generated pulses of the laser beam according to the inputs. However, the controller has been widely used including a processor, and thus detailed descriptions thereof will be omitted.

The interface may be configured to receive a user's control input, and configured to display information about a currently set state and use. The interface may for example be provided as a display unit with a touchscreen.

The controller may be configured to receive electric power from the outside and supply suitable power to electric components connected to the main body 10 and the handpiece 30.

The foot switch 40 is configured to be stepped on by a user to control the operations of the tattooing device. The foot switch 40 is configured to enable a user to control the operations of the tattooing device with his/her foot while both hands are used in holding and moving the tattooing device during a tattooing procedure.

The cable 20 is configured to transmit the electric power from the main body 10 to the handpiece 30 (to be described later), and a first side of the cable 20 may be supported on an arm extended from or connected to the main body 10 to prevent interference during the procedure.

The handpiece 30 may include a laser generator (not shown) and a lens (not shown). The laser generator is configured to receive electric power from the outside and generate a laser beam having a certain wavelength. The laser generator may emit a laser beam to fluid accommodated in a pressure chamber 100 (to be described later), so that the internal pressure of the pressure chamber 100 can be instantaneously increased. The wavelength of the laser beam emitted from the laser may be selected among various wavelengths of 532 nm, 1064 nm, 2900 nm, etc. For example, the laser generator may be configured to generate a laser beam having a wavelength of 2940 nm, of which the energy efficiency is the highest for water. However, such a wavelength of the laser beam generated by the laser generator is merely an example, and may be variously selected in consideration of the properties of the liquid in the pressure chamber 100. Meanwhile, the lens (not shown) is configured to condense the laser beam emitted from the laser generator, and, for example, the laser beam may be focused on the inner space of the pressure chamber when the tip 1 for injecting tattoo dye (to be described later) is mounted to the handpiece 30.

The tip 1 for injecting tattoo dye may be mounted at the end of the handpiece 30. The tip 1 for injecting tattoo dye may be structured to be easily mounted to and separated from the handpiece 30, and may be replaced with another tip according to users or according to the kinds and colors of tattoo dye. In other words, the tip for the tattoo dye may be selected as requested by a user and mounted at the end of the handpiece 30. The tip 1 for injecting tattoo dye may be irradiated with the foregoing laser beam so as to be internally increased in pressure. The tip 1 for injecting tattoo dye may be configured to inject the dye through a nozzle based on the pressure generated therein, so that the injected dye can be injected into a skin of human skin. The nozzle has an injecting hole 272, the inner diameter of which is within a predetermined range to inject the dye into the skin when the dye is injected at high pressure while minimizing the pain of a person who undergoes the procedure.

Meanwhile, the elements of the tip 1 for injecting tattoo dye will be described in detail with reference to FIGS. 2 to 11.

Figure 2:
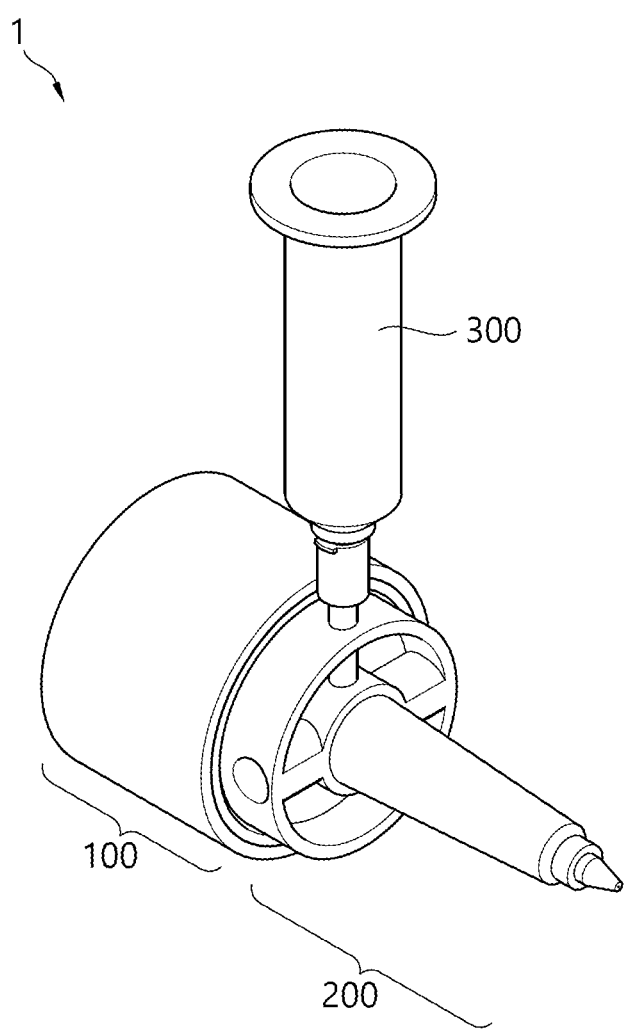
FIG. 2 is a perspective view of a tip for injecting tattoo dye.

FIG. 2 is a perspective view of the tip 1 for injecting tattoo dye.

Referring to FIG. 2, the tip 1 for injecting tattoo dye according to an embodiment of the disclosure is configured to inject the dye temporarily accommodated therein by the pressure generated when irradiated with the laser beam.

The tip 1 for injecting tattoo dye according to the disclosure may include the pressure chamber 100, a dye chamber 200, a dye supply unit 300, and a nozzle cap 400.

The size of the tip 1 for injecting tattoo dye may be suitable for a user to precisely position and use the tip 1 during the tattooing procedure. For example, the tip 1 may have an outer appearance shaped like a cylinder, the diameter of which ranges from 1 to 5 cm to be easily gripped by a user.

Each of the pressure chamber 100 and the dye chamber 200 may approximately be rotationally symmetric, and the pressure chamber 100 and the dye chamber 200 may be connected to each other in a direction of a rotationally symmetric axis.

The dye supply unit 300 is configured to store dye therein and continuously supply the dye to the dye chamber 200 as the dye accommodated in the dye chamber 200 is used. The dye supply unit 300 is configured to naturally move the dye to the dye chamber 200 based on difference between the internal pressure of the dye chamber 200 and the internal pressure of the dye supply unit 300. The dye supply unit 300 may for example have a cylindrical shape, and may include a slider valve 310 that seals the inside of the cylinder to continuously supply the dye while maintaining the internal pressure equal to the atmospheric pressure. The slider valve 310 may naturally move toward a dye valve as the dye in the cylinder moves outwards, i.e., toward the dye chamber 200.

Therefore, the dye supply unit 300 is prevented from being contaminated from the outside, and stably supplies the dye.

The nozzle cap 400 is configured to temporarily accommodate the dye not to leak out when the dye is injected into and fully filled in the dye chamber 200. The nozzle cap 400 may include a filter (not shown) placed therein. The filter may be configured to pass gas but filter liquid. When dye is injected into the dye chamber 200, the filter first discharges air filled in the dye accommodating space, and then filters the dye injected out of an inject nozzle 270 after the dye accommodating space is fully filled with the dye. Therefore, it is possible to prevent contamination from the outside when the tip 1 for injecting tattoo dye is initially filled with the dye. Meanwhile, when the dye leaks from the inject nozzle 270, a user may determine that the dye is completely injected into the dye chamber 200. Then, the nozzle cap 400 is removed when the tip 1 for injecting tattoo dye is used for the tattooing procedure.

Figure 3:
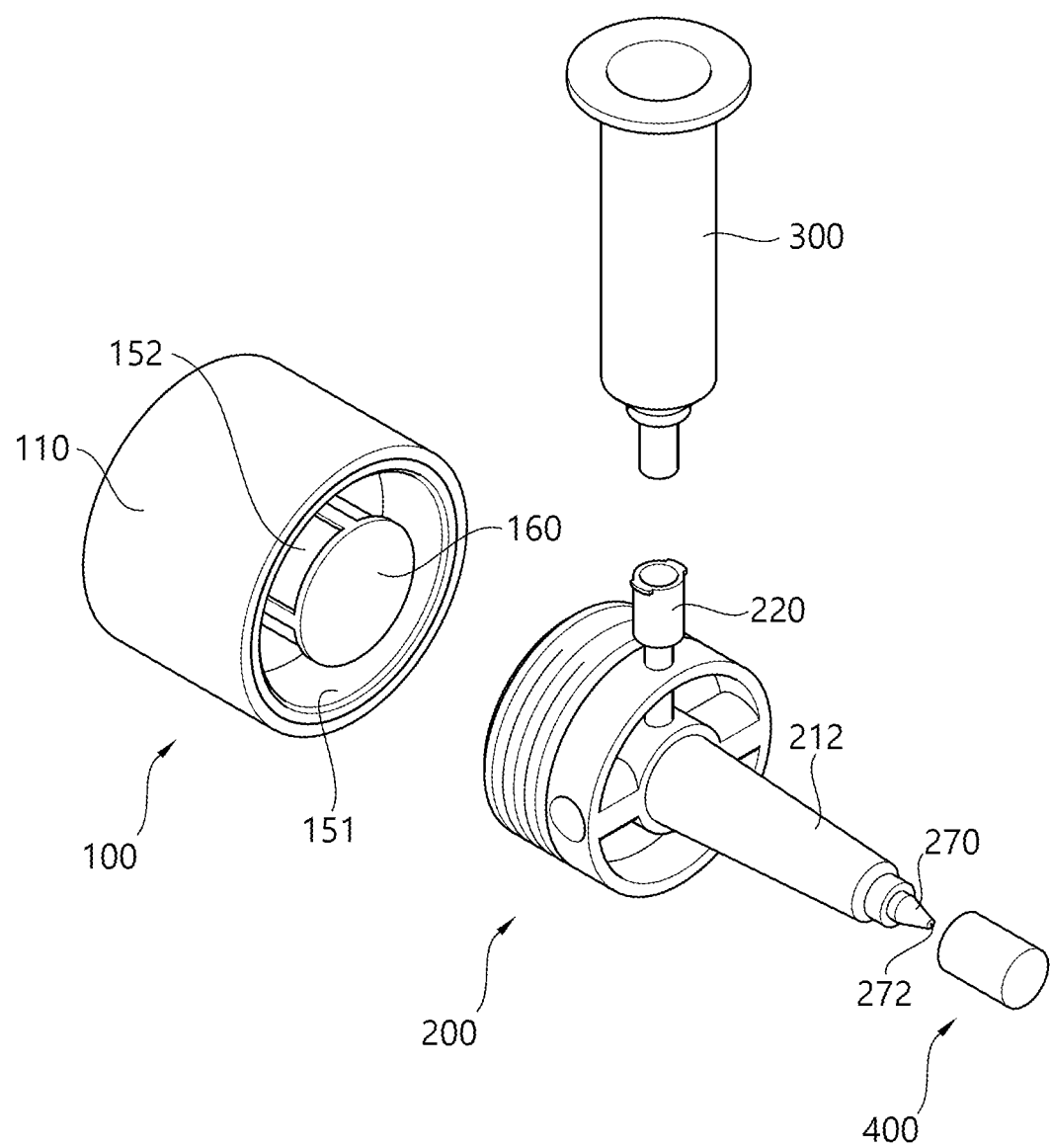
FIG. 3 is an exploded perspective view of a tip for injecting tattoo dye.

FIG. 3 is an exploded perspective view of the tip 1 for injecting tattoo dye.

Referring to FIG. 3, the pressure chamber 100 may be connected to the dye chamber 200, and the pressure chamber 100 and the dye chamber 200 may be configured to interactively affect their internal pressures when they are connected to each other. The dye chamber 200 and the pressure chamber 100 may have screw threads or the like publicly known coupling structure to be connected to each other. Further, female/male coupling structures may be respectively provided in the dye chamber 200 and the pressure chamber 100, thereby facilitating the coupling therebetween. For example, the pressure chamber 100 and the dye chamber 200 may respectively include a first connector 151 and a second connector 211, which will be described later.

The dye supply unit 300 may be configured to be connected to a connection port provided at a first side on a lateral surface of the dye chamber 200 so as to prevent interference when a user grips the tip 1 for injecting tattoo dye. The dye supply unit 300 is configured to be easily replaced with a new dye supply unit 300 when the dye stored therein is used up.

Below, the structure of the pressure chamber will be described in detail with reference to FIGS. 4 and 5.

Figure 4:
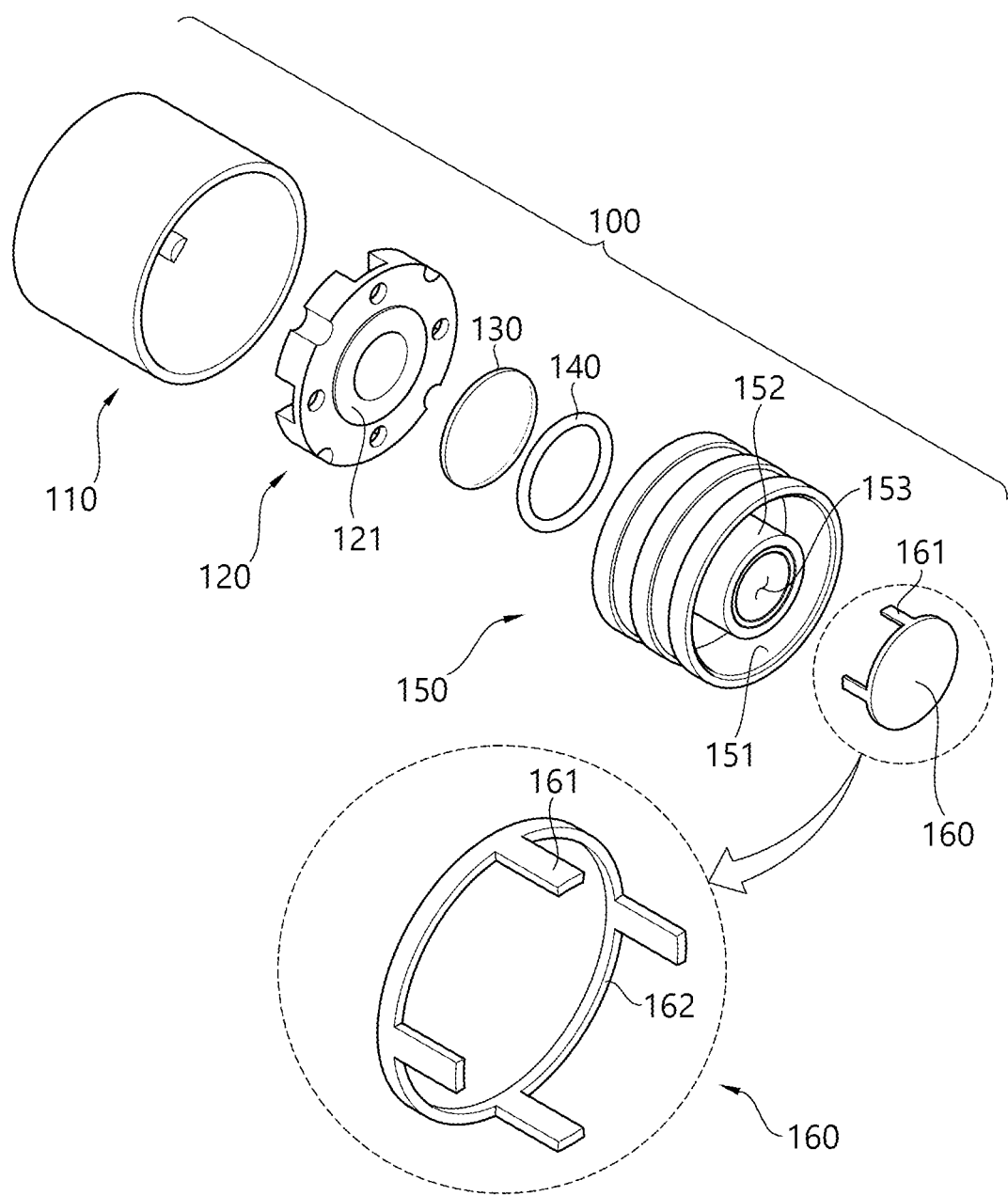
FIG. 4 is an exploded perspective view of a pressure chamber.
Figure 5:
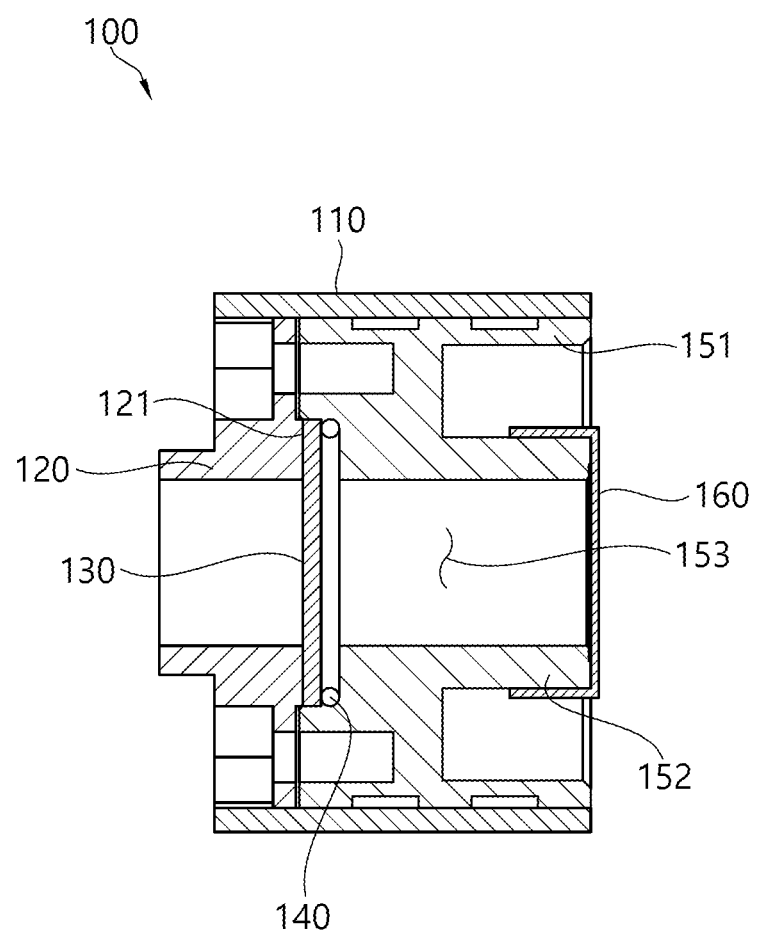
FIG. 5 is a cross-sectional view of a pressure chamber.

FIG. 4 is an exploded perspective view of the pressure chamber 100, and FIG. 5 is a cross-sectional view of the pressure chamber 100.

Referring to FIG. 4, the pressure chamber 100 may include a shield 110, an upper cap 120, a window 130, an O-ring 140, a pressure chamber housing 150, and a membrane unit 160.

The shield 110 is configured to generally prevent an impact applied from the outside, and improve a user's grip feeling. The shield 110 may for example be shaped like a hollow configured to surround the lateral side of the pressure chamber housing 150 (to be described later), and may be made of an elastic material.

The upper cap 120 may be coupled to the pressure chamber housing 150 (to be described later), and may be configured to firmly hold the window 130 and the O-ring 140. The upper cap 120 may be generally shaped like a disc, and formed with holes at a center portion to pass the laser beam therethrough. The upper cap 120 may couple with the pressure chamber housing 150 in the direction of the rotationally symmetric axis. The upper cap 120 may have a first side surface formed with a protrusion 121 to press the window 130 and the O-ring 140. On the other hand, the upper cap 120 may have a second side surface provide with a connection structure to which the handpiece 30 is connected from the outside. Meanwhile, such a structure of the upper cap 120 is merely an example, and the upper cap 120 may have various structures for making the window 130 and the O-ring 140 be in close contact with the pressure chamber housing 150.

The window 130 is configured to pass the laser beam coming from the outside. The window 130 may be made of a material appropriately strong enough not to be damaged even when the internal pressure of the pressure chamber 100 is increased by the liquid. The window 130 may for example be made of sapphire glass.

The O-ring 140 is provided between the window 130 and the pressure chamber housing 150 (to be described later) to prevent the liquid accommodated in the pressure chamber housing 150 from leaking out toward the lens. The O-ring 140 may have a widely used configuration, and thus detailed descriptions thereof will be omitted.

The pressure chamber housing 150 may have an inner space 153 to accommodate liquid therein. The pressure chamber housing 150 is provided with the inner space 153, and may include a membrane supporter 152 and the first connector 151.

The inner space 153 is placed in a central portion of the pressure chamber housing 150 so that the laser beam passed through the window 130 can reach the liquid. The pressure chamber housing 150 may generally be rotationally symmetric, and may be provided with the inner space 153 in the central portion thereof. The inner space 153 of the pressure chamber housing 150 is opened facing toward the dye chamber 200 (to be described later), and its opened portion may be sealed by the membrane unit 160 (to be described later).

The first connector 151 may be provided on an outer side of the pressure chamber housing 150 along a circumferential direction so as to connect with the dye chamber 200 (to be described later). The dye chamber 200 (to be described later) may be provided with the second connector 211 to couple with the first connector 151 so that the pressure chamber 100 and the dye chamber 200 can be connected to each other.

The membrane supporter 152 may be shaped like a hollow forming the inner space 153 and extended a predetermined length in the direction of the rotationally symmetric axis. The membrane supporter 152 may have an end portion facing toward the dye chamber 200 to support the membrane unit 160 in a thickness direction.

The pressure chamber housing 150 may be made of a material, the strength of which is relatively greater than that of the membrane unit 160, so that change in shape due to the increased internal pressure can be focused on the membrane unit 160 (to be described later) when the internal pressure of the pressure chamber housing 150 is increased.

The membrane unit 160 is configured to seal the inner space 153 of the pressure chamber housing 150, and transfer the pressure to a second side, i.e., to a dye accommodating space 230 in the dye chamber 200 as transformed when the inner space 153 is increased in pressure. The membrane unit 160 may include a membrane, a membrane cap, and a membrane guide.

The membrane is shaped like a disc, and has a first side facing the inner space 153 and a second side to be in contact with the dye accommodating space 230 of the dye chamber 200 (to be described later).

The membrane cap may be configured to partially surround the membrane supporter 152 of the pressure chamber housing 150. A user fully fills the inner space 153 with liquid, and then covers the membrane supporter 152 with the membrane unit 160. In this case, due to surface tension, the liquid may be a little convexedly filled in the inner space 153 and protrude more than the end of the membrane supporter 152. When the membrane supporter 152 in this state is covered with the membrane unit 160, the membrane cap 162 seals the inner space 153 while preventing gas from flowing into the inner space 153.

A membrane guide 161 may be formed a predetermined length in a direction perpendicular to the membrane. The membrane guide 161 may guide the membrane unit 160 to a sealing position when a user installs the membrane unit 160 to the membrane supporter 152.

Below, the dye chamber 200 will be described in detail with reference to FIGS. 6 to 8.

Figure 6:
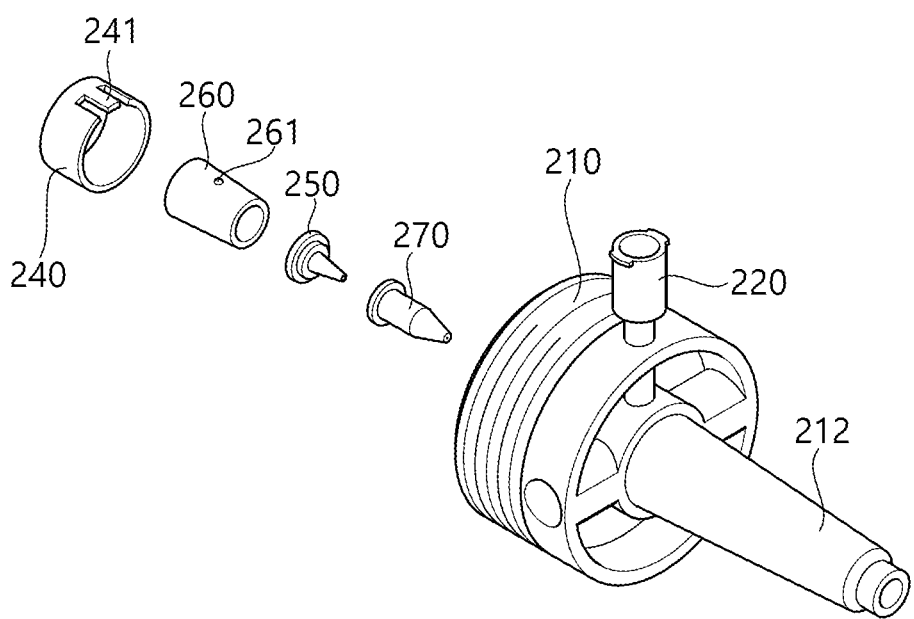
FIG. 6 is an exploded perspective view of a dye chamber.
Figure 7:
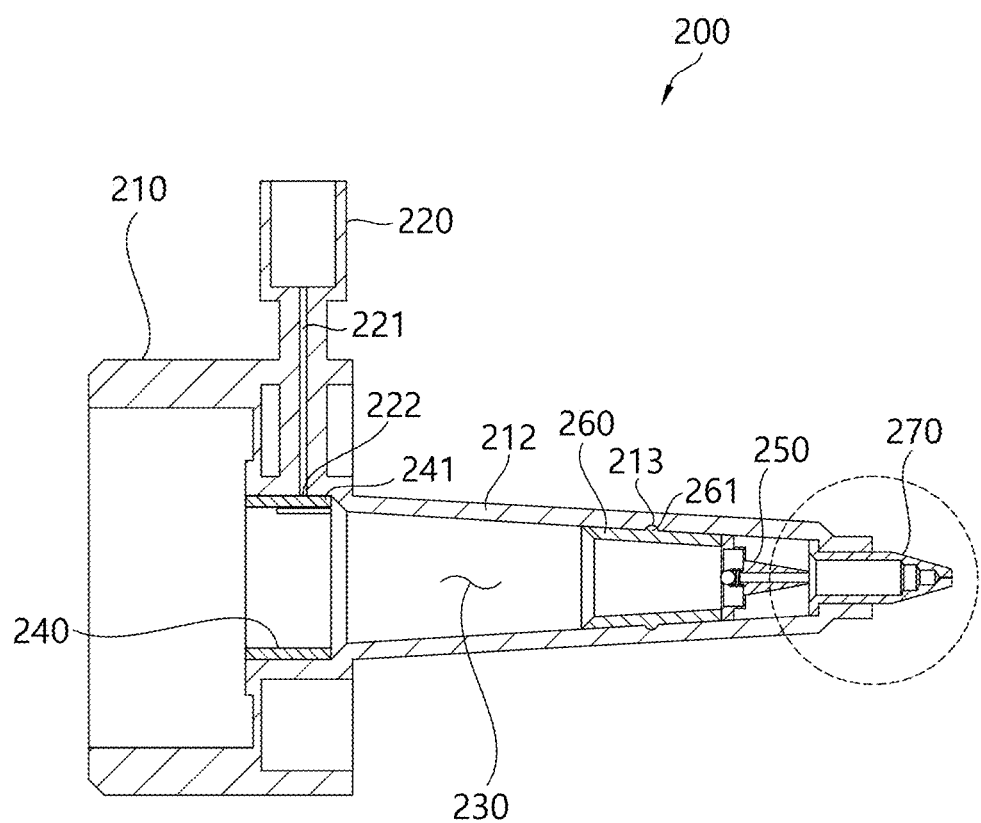
FIG. 7 is a cross-sectional view of a dye chamber.
Figure 8:
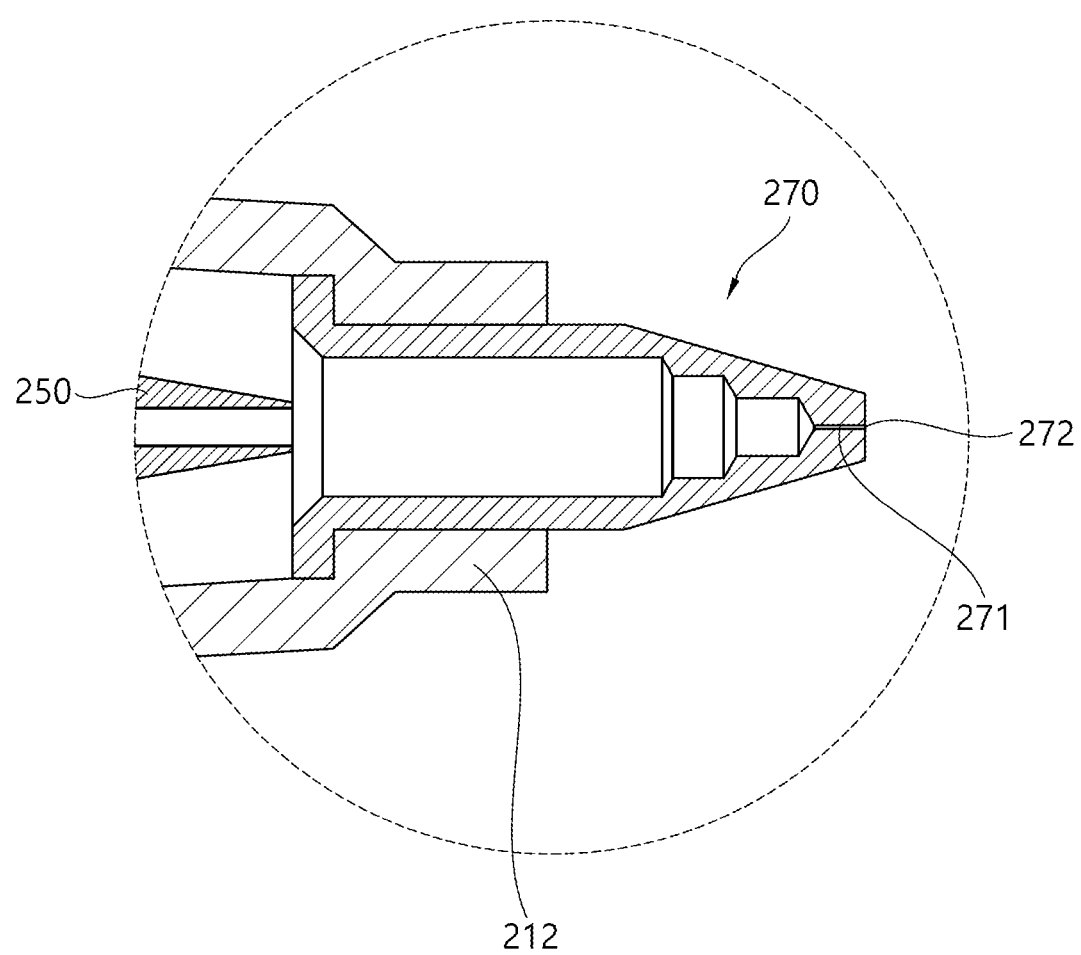
FIG. 8 is an enlarged exploded perspective view of an inject nozzle.

FIG. 6 is an exploded perspective view of the dye chamber 200, FIG. 7 is a cross-sectional view of the dye chamber 200, and FIG. 8 is an enlarged exploded perspective view of the inject nozzle 270.

As shown therein, the dye chamber 200 may include a dye chamber housing 210, the dye accommodating space 230, a connection port 220, a channel 221, a first valve 240, a second valve 250, a stopper 260, and the inject nozzle 270.

The dye chamber housing 210 is structured to accommodate dye in the dye chamber 200, and used as a base on which the other elements of the dye chamber 200 are provided.

The dye chamber housing 210 is generally rotationally symmetric, and has a first side, to which the foregoing pressure chamber 100 is connected, and a second side, in which the inject nozzle 270 is provided to inject dye as the internal pressure increases, along a rotation central axis. The dye chamber housing 210 may include an extended portion 212 extended in the direction of the rotation central axis so as to have the inject nozzle 270. The extended portion 212 may be shaped like a hollow cone, and allow the dye to move therein.

The dye accommodating space 230 may be configured to accommodate therein the dye, which will be used for tattooing, and may be a part of the inner space of the dye chamber housing 210.

The connection port 220 may be configured to connect with the foregoing dye supply unit 300, and may be provided on the first side surface of the dye chamber housing 210. The connection portion 220 may be configured to easily couple with and separate from the dye supply unit 300.

The channel 221 may be formed penetrating the dye chamber housing 210 in a radial direction of the rotational symmetry so that the dye can flow in the connection port 220 and the dye accommodating space 230. Therefore, fluid communication is achieved between the dye supply unit 300 and the dye accommodating space through the channel 221. The d has a first side formed from an opening 222 at the lateral side of the dye accommodating space 230, and a second side connected up to the opening 222 formed at an end portion of the connection port 220.

The first valve 240 may be configured to set the direction of the dye flowing from the dye supply unit 300 into the dye accommodating space 230. The first valve 240 may for example be configured to make the dye flow from the dye supply unit 300 toward the dye accommodating space 230. The first valve 240 may for example be shaped like a hollow and fitted to the inner wall of the dye accommodating space 230. The first valve 240 may include an opening/closing portion 241 at a first side to open and close the opening 222 of the channel 221 formed in the inner wall of the dye accommodating space 230. The opening/closing portion 241 may be cut in the form of a pair of notches on the hollow-shaped first side and may be bent by external force.

When the first valve 240 is provided in the dye accommodating space 230, the opening 222 of the channel 221 may be closed by the opening/closing portion 241. Meanwhile, when force based on the internal pressure of the channel 221 is greater than resistance based on the internal pressure of the dye accommodating space 230 and resilience based on the elasticity of the opening/closing portion 241, the opening/closing portion 241 may be bent toward the dye accommodating space 230 so that the dye can flow from the channel 221 toward the dye accommodating space 230.

However, such a configuration of the first valve 240 is merely an example, and the first valve 240 may alternatively be provided as a one-way valve or a check valve to make the dye flow from the dye supply unit 300 to the dye accommodating space 230.

The second valve 250 may be configured to set the direction of the dye flowing from the dye accommodating space 230 toward the inject nozzle 270. The second valve 250 may be provided as inserted in a space formed inside the extended portion 212 of the foregoing dye chamber housing 210. The second valve 250 may be configured as a one-way valve by which the dye is allowed to flow toward the inject nozzle 270 in the direction of the rotationally symmetric axis but prevented from flowing in the reverse direction. The second valve 250 may for example be provided as a check valve including a ball and a spring. However, the check valve is merely an example, and the second valve 250 may alternatively be provided as various configurations for setting the flowing direction.

The stopper 260 may be configured to stably lock the foregoing second valve 250 inside the extended portion 212. The stopper 260 may have a tapering shape, in which the diameter of a first side end portion is gradually decreased, corresponding to the inner space of the extended portion 212. The stopper 260 may include a stopper locking portion 261 protruding from one side of the outer surface thereof and firmly locked to the inner surface of the extended portion 212, and the extended portion 212 may include a stopper locking groove 213 formed on the inner surface thereof and corresponding to the stopper locking portion 261.

The inject nozzle 270 is configured to inject the dye outwards. One side of the inject nozzle 270 may be connected to the extended portion 212 of the foregoing dye chamber housing 210. The end portion of the inject nozzle 270 may be cut to have a plane surface not to be inserted into skin even though it comes into contact with the skin. The inject nozzle 270 may include an inject channel 271 formed at a central side thereof, and an inject hole formed at the end portion thereof to inject the dye passed through the inject channel 271. The inject hole may be formed to have an inner diameter of, for example, 500 µm to 50 µm, and may be internally subjected to a coating to make the dye smoothly flow. Meanwhile, the inject nozzle 270 may be configured to inject a uniform amount of dye even in repeatedly use. For example, the inject nozzle 270 may be made of metal.

Below, the operations of the tip 1 for injecting tattoo dye according to the disclosure will be described in detail with reference to FIGS. 9 and 10.

Figure 9:
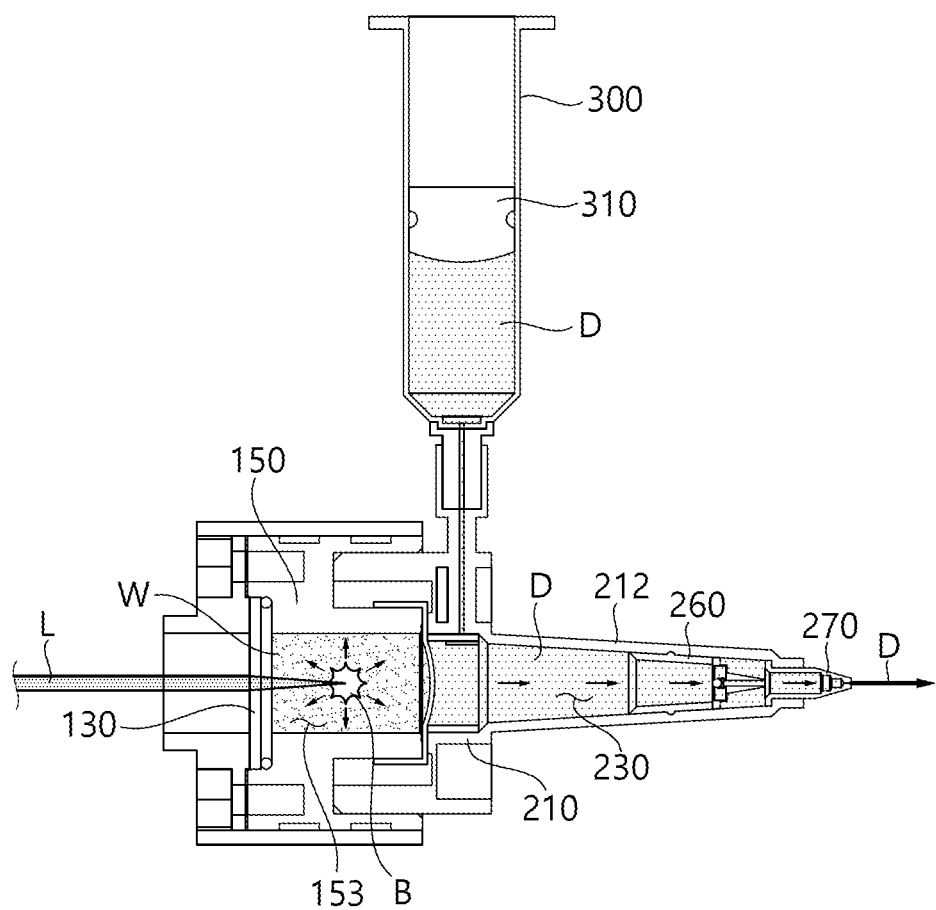
FIG. 9 is an operating state view when a tip for injecting tattoo dye injects dye.
Figure 10:
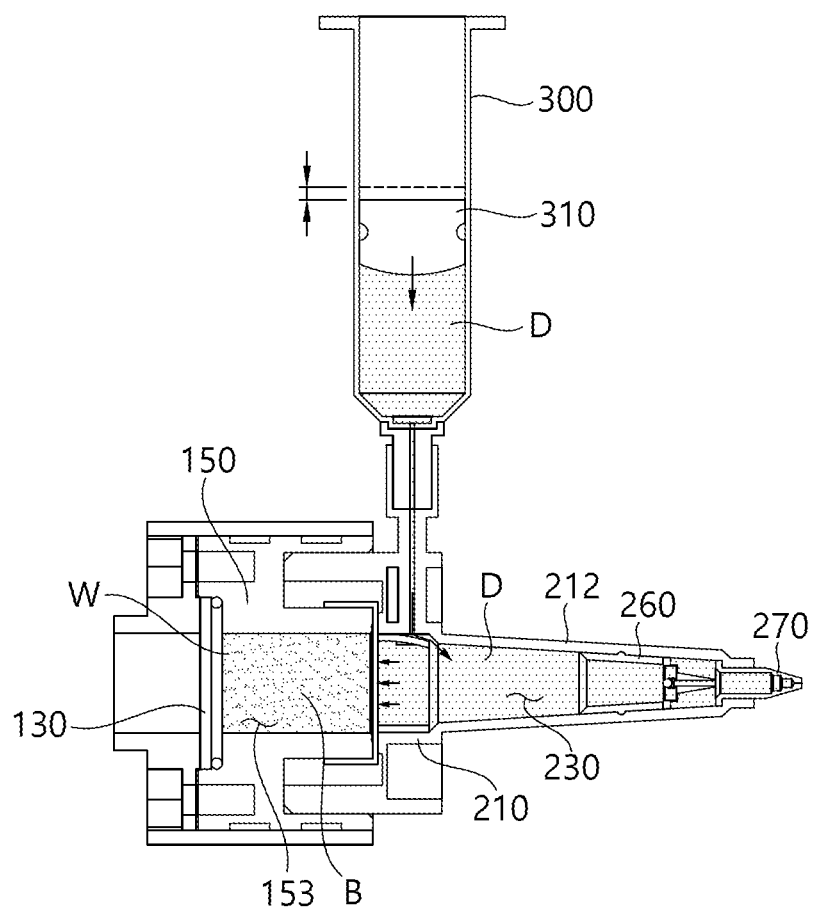
FIG. 10 is an operating state view immediately after a tip for injecting tattoo dye injects dye.

FIG. 9 is an operating state view when the tip 1 for injecting tattoo dye injects dye, and FIG. 10 is an operating state view immediately after the tip 1 for injecting tattoo dye injects dye.

Referring to FIG. 9, the tip 1 for injecting tattoo dye may be used with the dye supply unit 300 connected thereto, and the handpiece 30 may be connected to the first side of the pressure chamber 100. However, the illustration of the handpiece 30 is partially omitted for convenience of description.

First, when the tip 1 for injecting tattoo dye is used, the inner space 153 of the pressure chamber 100 is fully filled with liquid, e.g., water W, in which hot water of 20° C. to 80° C. may be used to minimize the generation of bubbles. Meanwhile, the dye accommodating space 230 is also fully filled with the dye D to make ready for the operation.

Then, when a user makes an input, for example, steps on the foot switch 40 to apply the pulses of a laser beam L, the laser beam causes bubbles B to be generated inside the pressure chamber 100 and the generation of bubbles instantaneously increase the internal pressure of the pressure chamber 100. Then, the pressure increased inside the pressure chamber 100 causes the membrane unit 160 to be transformed toward the dye accommodating space 230, thereby transferring the pressure to the dye accommodating space 230. When the pressure is increased inside the dye accommodating space 230, the dye D is injected through only one outlet, i.e., the inject nozzle 270.

Referring to FIG. 10, after the dye D is injected by one application of the laser beam, the bubbles B generated inside the inner space 153 of the pressure chamber 100 disappear and the pressure is decreased. Further, the membrane unit 160 returns toward the inner space 153, and thus the pressure inside the dye accommodating space 230 is momentarily decreased. In this case, the pressure inside the dye accommodating space 230 is momentarily lower than the pressure inside the channel 221, and thus the first valve 240 is opened so that the dye D can flow from the channel 221 to the dye accommodating space 230, thereby refilling the dye accommodating space 230 with the dye as much as injected out once. In this case, the second valve 250 prevents air and foreign materials from being introduced from the inject nozzle 270 into the dye accommodating space 230, so that the pressure decreased inside the dye accommodating space 230 is entirely used in moving the dye D from the dye supply unit 300 to the dye accommodating space 230.

Below, an alternative example of the inject nozzle 270 will be described with reference to FIG. 11.

Figure 11:
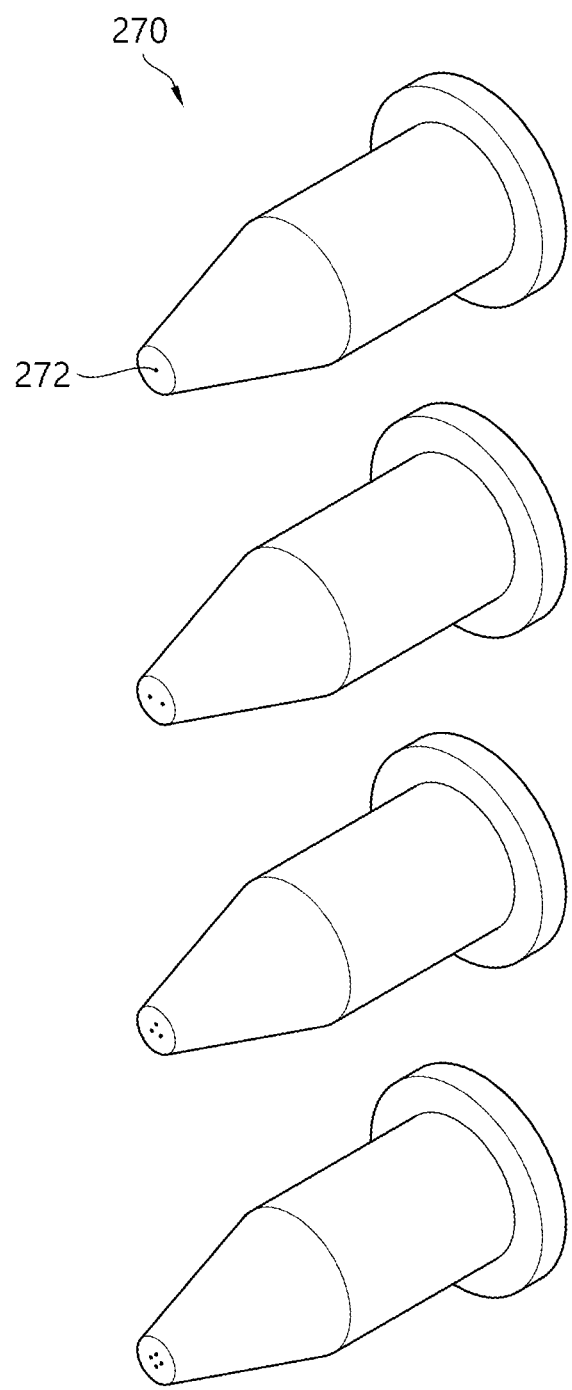
FIG. 11 is a view showing an alternative example of an inject nozzle.

FIG. 11 is a view showing an alternative example of an inject nozzle.

As shown therein, the number of injecting holes 272 in the inject nozzle 270 and each diameter of injecting holes 272 may be variously set. When the number of injecting holes 272 is increased, the pressure change inside the pressure chamber 100 is taken into account to set the total cross-sectional areas of the channels the injecting holes 272 have and set the arrangement of the injecting holes 272. However, this is merely an example, and the number and diameter of injecting holes 272 may be variously combined.

Below, the tip 1 for injecting tattoo dye according to another embodiment of the disclosure will be described with reference to FIGS. 12 to 14. Meanwhile, this embodiment may also include the same elements as those described in the foregoing embodiments, and therefore different elements will be described in detail without describing the same elements to avoid repetitive descriptions.

Figure 12:
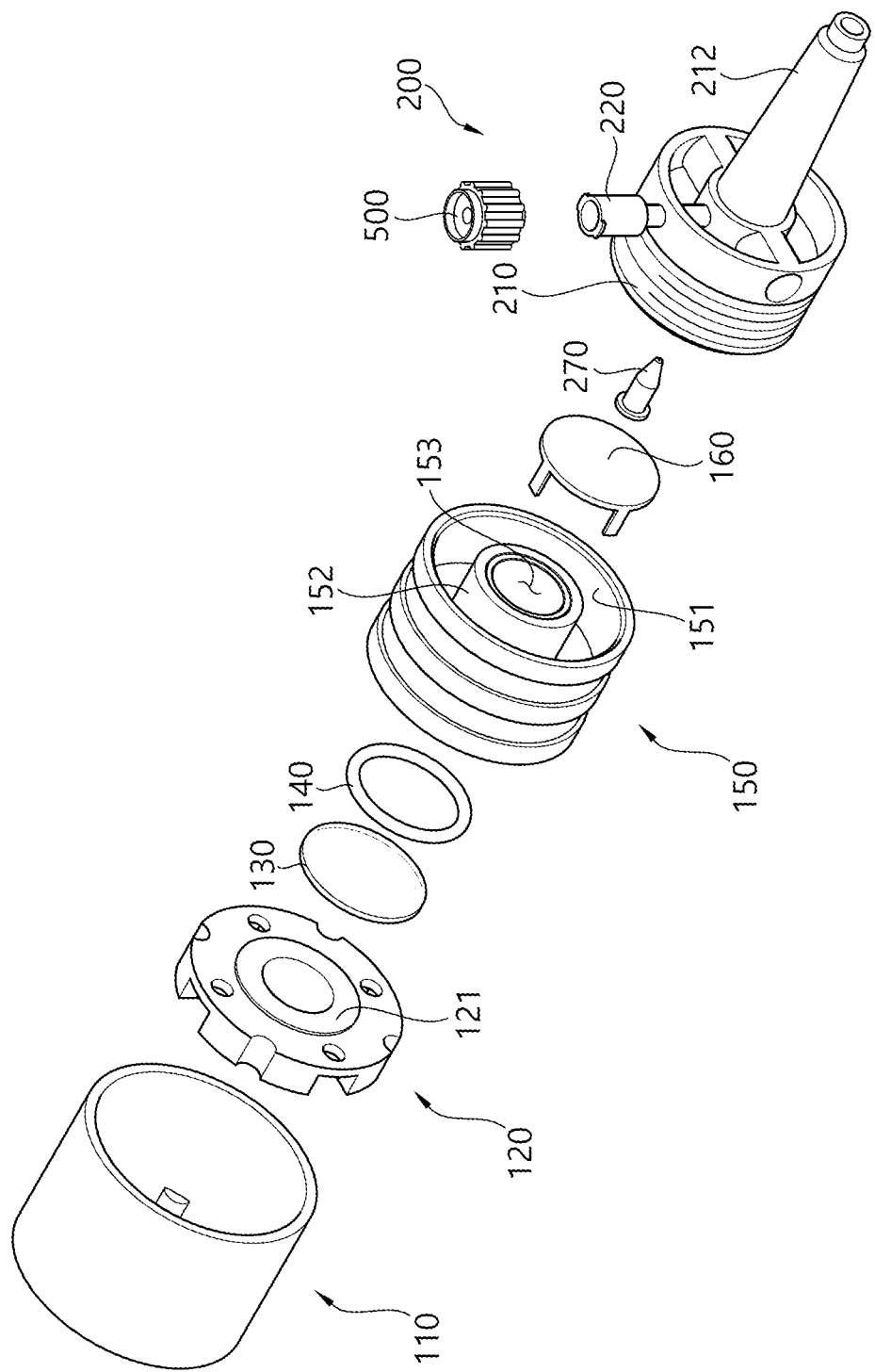
FIG. 12 is an exploded perspective view of a tip for injecting tattoo dye according to another embodiment.
Figure 13:
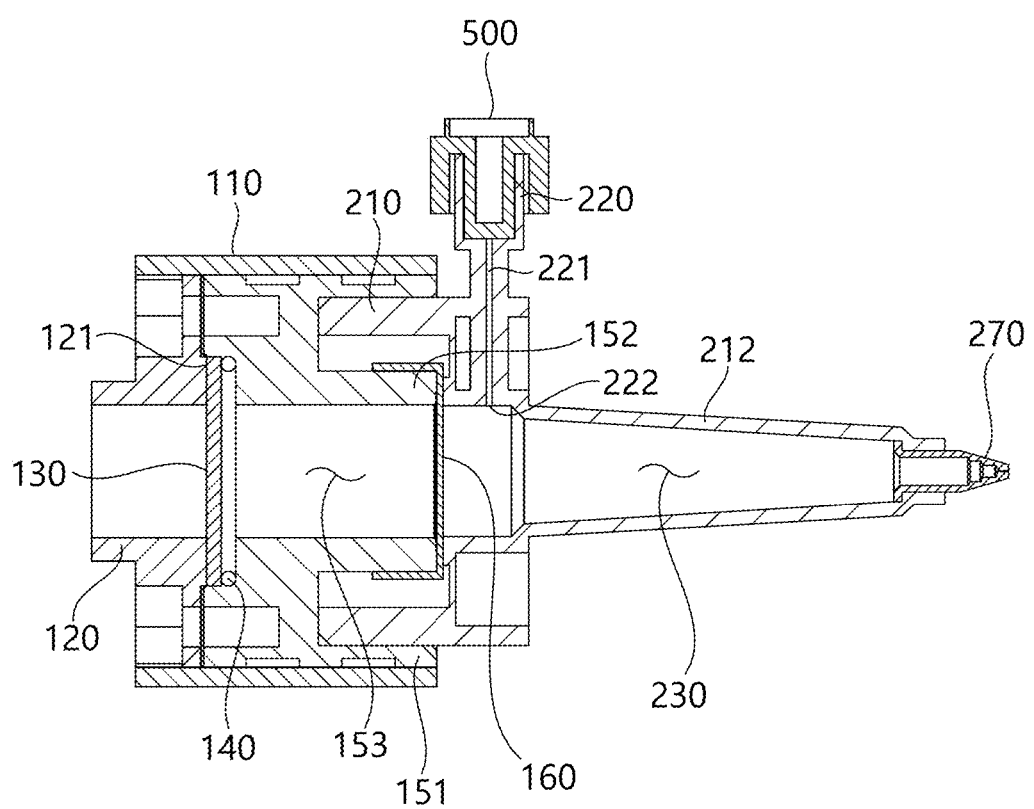
FIG. 13 is a cross-sectional view of the embodiment shown in FIG. 12.

FIG. 12 is an exploded perspective view of a tip for injecting tattoo dye according to another embodiment, and FIG. 13 is a cross-sectional view of the embodiment shown in FIG. 12.

Unlike the foregoing embodiments, the tip 1 for injecting tattoo dye according to this embodiment is configured to be directly used by a user in the state that the dye chamber 200 is filled with the dye. In this embodiment, the dye chamber 200 may include the dye chamber housing 210, the connection port 220, a connection port cap 500, and the inject nozzle 270.

The dye chamber housing 210 may be configured similarly to that of the foregoing embodiment, and may include a space to accommodate dye therein.

In this embodiment, the connection port 220 may couple with the connection port cap 500. First, a user may inject the dye D through the connection port 220. When the dye is filled in the dye accommodating space through the connection port 220, a user stops injecting the dye and seals up the connection port 220 with the connection port cap 500.

Figure 14:
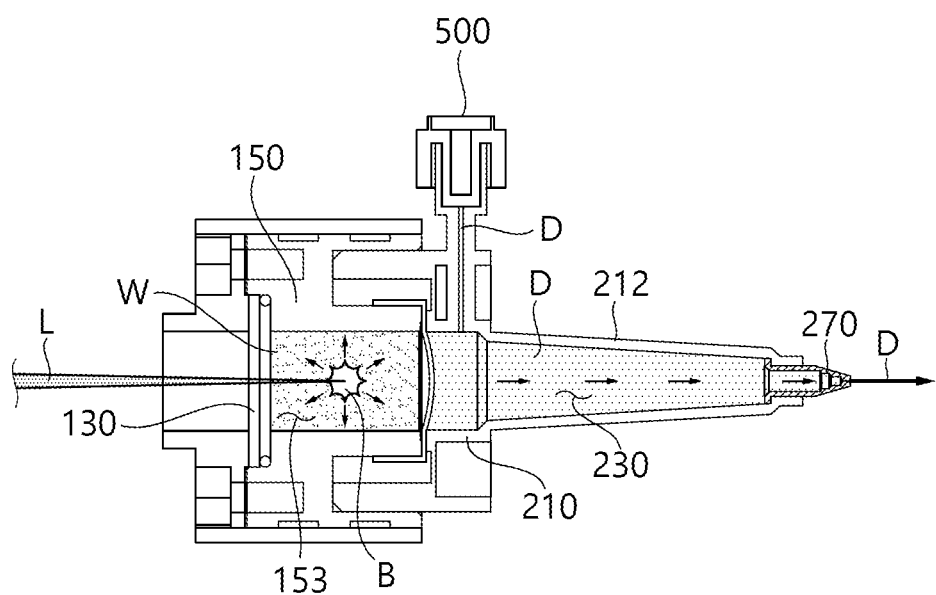
FIG. 14 is an using state view of the embodiment shown in FIG. 12.

FIG. 14 is an using state view of the embodiment shown in FIG. 12. As shown therein, the dye D may be accommodated in the connection port 220, i.e., in the channel 221 and the dye accommodating space 230. The connection port 220 may be sealed up with the connection port cap 500. Similarly to the foregoing embodiments, when the pressure chamber 100 is irradiated with the laser beam L and increased in pressure, the pressure may be transferred to the dye accommodating space 230 by the membrane unit 160. As the pressure of the dye accommodating space 230 is increased, the dye may be finally discharged through only one outlet, i.e., the inject nozzle 270.

As described above, the tip for injecting tattoo dye according to the disclosure can inject the dye at high pressure without a needle, thereby having effects on relieving pain of a person who is getting tattoo, and carrying out a tattooing procedure hygienically.

Further, the tip for injecting tattoo dye according to the disclosure can inject a fixed amount of dye at each inject. In addition, the tip for injecting tattoo dye has an effect on preventing external foreign materials from being introduced thereinto through the inject nozzle.

The invention claimed is:
1. A tip for injecting tattoo dye, comprising:
a pressure chamber configured to accommodate liquid therein;
a window provided at a first side of the pressure chamber, and configured to allow a laser beam emitted from an outside to pass therethrough and reach the liquid accommodated in the pressure chamber;
a membrane unit provided at the opposite side of the pressure chamber from the window, and configured to seal the pressure chamber and be transformed by pressure generated as the liquid is irradiated with the laser beam;
a dye chamber defining a dye loading space which is configured to accommodate tattoo dye, an opened portion of the dye chamber being sealed by the membrane unit;
a dye supply unit configured to supply the dye to the dye loading space;
a first valve configured to set whether to allow the dye to flow from the dye supply unit to the dye chamber; and
an inject nozzle provided at one end of the dye chamber, and configured to inject the dye accommodated in the dye loading space outwards,
wherein the dye chamber comprises a channel formed on an inner wall for fluid communication with the dye supply unit,
wherein the first valve comprises an opening/closing portion to come into close contact with and seals an opening on a side of the channel,
wherein the dye chamber is internally formed with a cylindrical space, wherein the opening/closing portion is made of an elastic material, wherein the first valve has a hollow shape and comprises an outer circumferential surface to come into close contact with an inner surface of the dye chamber, and wherein the opening/closing portion is defined between two notches on the first valve.

2. The tip for injecting tattoo dye of claim 1, wherein, pressure in the pressure chamber is increased by laser pulses, the membrane unit transfers the pressure from the pressure chamber to the dye loading space, and the dye is injected due to the increased pressure inside the dye loading space.

3. The tip for injecting tattoo dye of claim 2, further comprising a second valve provided inside the dye chamber, and configured to set whether to allow the dye to flow toward the inject nozzle.

4. The tip for injecting tattoo dye of claim 3, wherein the second valve comprises a one-way valve.

5. The tip for injecting tattoo dye of claim 4, further comprising a stopper configured to press the second valve toward the inject nozzle so that the second valve can be locked in the dye chamber.

6. The tip for injecting tattoo dye of claim 5, wherein the stopper is internally formed with a hollow to allow the dye to move from an inside of the dye chamber to the inject nozzle.

7. The tip for injecting tattoo dye of claim 2, wherein the dye supply unit comprises a slider valve.

* * * * *